US00PP24721P2

(12) United States Plant Patent
Giesen

(10) Patent No.: US PP24,721 P2
(45) Date of Patent: Jul. 29, 2014

(54) *LOBELIA* PLANT NAMED 'LOBZ0004'

(50) Latin Name: *Lobelia erinus*
Varietal Denomination: LOBZ0004

(75) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 170 days.

(21) Appl. No.: 13/507,411

(22) Filed: Jun. 26, 2012

(51) Int. Cl.
*A01H 5/00* (2006.01)

(52) U.S. Cl.
USPC ..... Plt./451

(58) Field of Classification Search
CPC ..... A01H 5/02
USPC ..... Plt./451
See application file for complete search history.

*Primary Examiner* — June Hwu
(74) *Attorney, Agent, or Firm* — Joshua L. Price

(57) ABSTRACT

A new *Lobelia* plant named 'LOBZ0004' particularly distinguished by the large light blue and white bi-color flowers, medium green foliage, and a vigorous well branched, upright and mounded plant habit.

1 Drawing Sheet

Latin name of the genus and species of the plant claimed: *Lobelia erinus.*

Varietal denomination: 'LOBZ0004'.

BACKGROUND OF THE NEW PLANT

The present invention comprises a new *Lobelia*, botanically known as *Lobelia erinus*, and hereinafter referred to by the variety name 'LOBZ0004'.

'LOBZ0004' is a product of a planned breeding program. The new cultivar has large violet-blue flowers, medium green foliage, and a vigorous well branched, upright, and mounded plant habit.

'LOBZ0004' originated from a hybridization made in January 2007 in Andijk, The Netherlands. The female parent was the unpatented, proprietary plant designated 'LOB06-235-2' with larger blue with a white eye flower color, and longer, darker green foliage than that of 'LOBZ0004'.

The male parent of 'LOBZ0004' was an unpatented, proprietary plant designated 'LOB03-117-1' with a smaller flower size and a white flower color, with shorter stems than that of 'LOBZ0004'. The seeds were sown in May 2007.

'LOBZ0004' was selected as one flowering plant within the progeny of the stated cross in May 2007 in a greenhouse in Andijk, The Netherlands.

The first act of asexual reproduction of 'LOBZ0004' was accomplished when vegetative cuttings were propagated from the initial selection in May 2007 in a greenhouse in Andijk, The Netherlands.

BRIEF SUMMARY OF INVENTION

Horticultural examination of plants grown from cuttings of the plant initiated in May 2007, and continuing thereafter, has demonstrated that the combination of characteristics as herein disclosed for 'LOBZ0004' are firmly fixed and are retained through successive generations of asexual reproduction.

'LOBZ0004' has not been observed under all possible environmental conditions. The phenotype may vary significantly with variations in environment such as temperature, light intensity, and day length.

A Plant Breeder's Right for this cultivar was applied for in Canada on Nov. 1, 2011, No. 11-7428. 'LOBZ0004' has not been made publicly available more than one year prior to the filing of this application.

The following traits have been repeatedly observed and are determined to be basic characteristics of the new variety. The combination of these characteristics distinguishes this *Lobelia* as a new and distinct variety.

BRIEF DESCRIPTION OF THE PHOTOGRAPHS

The accompanying photographic drawings show typical flower and foliage characteristics of 'LOBZ0004' with colors being as true as possible with an illustration of this type.

Figure 1:
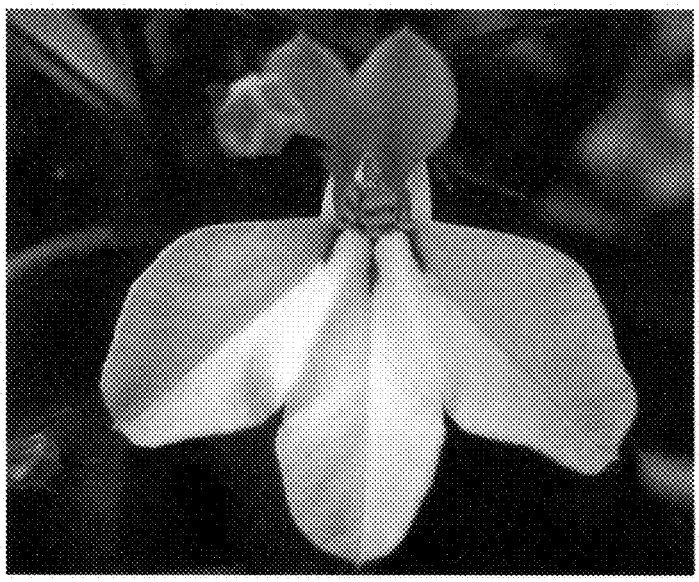
Figure 2:
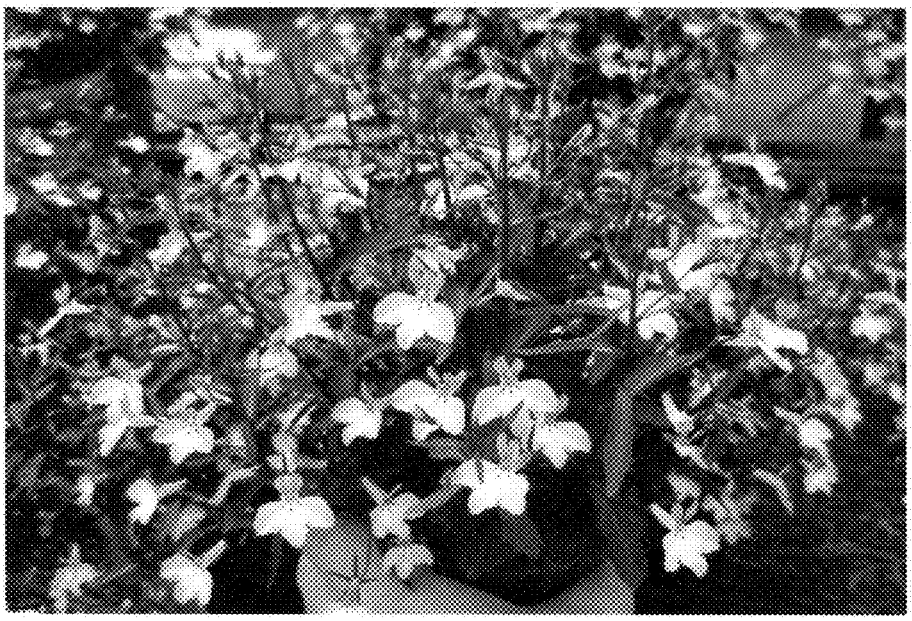

The photographic drawings show in FIG. 1 a close-up of the flower and in FIG. 2 a flowering plant of the new variety.

DETAILED BOTANICAL DESCRIPTION

The plant descriptions and measurements were taken in Gilroy, Calif. under natural light in May 2012. These plants were approximately 22-23 weeks old and were growing 5 plants in a 10 inch pot in greenhouse trials. The plants used for the photographs were about 14 weeks old, growing in a greenhouse trial in 10 cm pots, in Enkhuizen, The Netherlands. The photographs were taken in April 2012.

Color references are made to The Royal Horticultural Society Colour Chart (R.H.S.) 2001.

TABLE 1

DIFFERENCES BETWEEN THE NEW VARIETY 'LOBZ0004' AND A MOST SIMILAR VARIETY

| | 'LOBZ0004' | 'Wesloblue' (U.S. Plant Pat. No. 19,095) |
|---|---|---|
| Flower color: | Bi-color: white and lighter blue | Somewhat darker blue |

TABLE 1-continued

DIFFERENCES BETWEEN THE NEW VARIETY 'LOBZ0004' AND A MOST SIMILAR VARIETY

| | 'LOBZ0004' | 'Wesloblue' (U.S. Plant Pat. No. 19,095) |
|---|---|---|
| Flower size: | Larger | Smaller |
| Plant habit: | More upright habit | More spreading |

Plant:

*Form, growth and habit*.—Initially more upright, becoming more spreading and mounded; freely branched with strong and flexible lateral branching at every node. Pinching does enhance branching.

*Plant height*.—17.0-19.0 cm.

*Plant height* (*inflorescence included*).—20.0-24.0 cm.

*Plant width*.—About 20.0-25.0 cm.

Roots:

*Number of days to initiate roots and develop roots*.—21-24 days at about 22 degrees C.

*Type*.—Fine, fibrous, free branching.

*Color*.—RHS N155B but whiter.

Foliage:

*Arrangement*.—Alternate.

*Immature, leaf color, upper surface*.—Closest to RHS 137B.

*Lower surface*.—Closest to RHS 137C.

*Mature, leaf color, upper surface*.—Closest to RHS 137B.

*Lower surface*.—Closest to RHS 137C.

*Length*.—2.5-3.7 cm.

*Width*.—1.1-1.3 cm.

*Shape*.—Lanceolate.

*Base shape*.—Cuncate.

*Apex shape*.—Mucronulate.

*Margin*.—Dentate.

*Texture, upper surface*.—Slightly hirsute mostly on the basal margin.

*Lower surface*.—Slightly hirsute mostly on the basal margin.

*Color of veins, upper surface*.—Indistinct.

*Color of veins, lower surface*.—Indistinct.

*Pattern of veining*.—Pinnate.

Stem:

*Quantity of main branches per plant*.—10-15.

*Color of stem*.—RHS 137B.

*Length of stem*.—About 25.0 cm.

*Diameter*.—0.2 cm.

*Length of internodes*.—1.0-3.0 cm.

*Texture*.—Very sparsely hirsute.

Inflorescence:

*Type*.—Raceme, terminal (at stem end), composed of single flowers in an alternate arrangement, with one flower per node, subtended by a narrow leaflet.

*Blooming habit*.—Continuous through the growing season.

*Quantity of inflorescences per plant*.—About 150-200.

*Average number of flowers per raceme*.—16.

*Average size of the raceme*.—20 cm long.

*Lastingness of individual blooms on the plant*.—5-7 days depending on temperature.

*Fragrance*.—None.

*Color of peduncle*.—RHS 138A.

*Length of peduncle*.—About 15.0 cm.

*Peduncle diameter*.—0.2 cm.

*Texture*.—Glabrous.

*Color of pedicels*.—RHS 138A.

*Length of pedicels*.—2.5-3.0 cm.

*Diameter of pedicels*.—0.05-0.1 cm.

*Texture*.—Glabrous.

Bud (just when showing color):

*Color*.—RHS 157C on the underside and shades of RHS 90C on the upper side.

*Length*.—2.1-2.2 cm.

*Width*.—0.3-0.4 cm.

*Shape*.—Oblong or Tubular.

Corolla:

*Corolla type*.—Single, zygomorphic; upper lip has two smaller lobes and lower lip has three larger and broader lobes; lobes are fused at the base and slightly cupped.

Immature inflorescence:

*Flower width*.—1.7-1.8 cm when flattened out.

*Flower color, upper petals, upper surface*.—Between RHS 95C and RHS 95D with darker shades basally and at the apex.

*Lower surface*.—Closest to but lighter than RHS 96D.

*Color lower petals, upper surface*.—Blotchy shades lighter than RHS 95C, with a large basal patch closest to RHS 155C but whiter, and a bright spot of RHS 95B basally on the midvein and RHS 144A on the inner margin basal junction ridge.

*Lower surface*.—Closest but lighter than RHS 96D.

Mature inflorescence:

*Flower length*.—2.1-2.2 cm.

*Flower, width*.—2.1 cm.

*Color upper petals, upper surface*.—Lighter than RHS 95C and fading to closer to RHS 95D.

*Lower surface*.—Lighter than RHS 95D.

*Upper petals, length* (*from the corolla opening*).—0.9 cm.

*Upper petals, width*.—0.3 cm.

*Color lower petals, upper surface*.—RHS 95C fading to closer to RHS 95D with a large basal patch closest to RHS 155C but whiter, and a bright spot of RHS 95B basally on the midvein and RHS 144A on the inner margin basal junction ridge.

*Lower surface*.—Closer to RHS N155A but lighter.

*Lower petals, length* (*from the corolla opening*).—1.2 cm.

*Lower petals, width*.—0.7 cm.

Petal (lobes):

*Apex*.—Upper petals acute; lower petals rounded to weakly mucronulate.

*Base*.—Fused.

*Margin*.—Entire.

*Texture, upper surface*.—Papillose.

*Lower surface*.—Papillose.

*Corolla tube color, outside, upper surface*.—Closest to RHS 95D.

*Outside lower surface*.—Lighter than RHS 95D.

*Color inside*.—RHS 155C with between RHS 95C and RHS 95D markings.

*Corolla tube length*.—1.0-1.2 cm.

*Corolla tube width*.—0.4 cm at the widest.

Calyx:

*Quantity and form*.—5 sepals in a whorl, fuse at the base and somewhat funnel shaped.

*Color, upper surface*.—RHS 137B.

*Lower surface*.—RHS 137B.

*Length*.—1.0 cm.
*Width*.—0.075 cm.
*Shape*.—Ligulate.
*Apex shape*.—Acute.
*Base*.—Fused.
*Margins*.—Entire.
*Texture, upper surface*.—Glabrous.
*Lower surface*.—Glabrous.

Reproductive organs:

*Gynoecium*.—Pistil quantity: 1. Length: 0.8 cm. Style color: RHS 145C. Style length: 0.8-0.9 cm. Stigma color: RHS 147B with RHS N186C infused. Ovary color: RHS 157C. Ovary length: 0.2 cm. Ovary diameter: 0.2 cm.

*Androecium*.—Stamen quantity: 5. Color of filaments: RHS 155C. Length filaments: 0.8-0.9 cm. Anther color: RHS N187A. Anther length: 0.15 cm. Color of pollen: RHS 13C. Pollen amount: Normal. Fertility/seed set: Has not been determined to date. Disease/pest resistance: Has not been determined to date.

What is claimed is:

1. A new and distinct variety of *Lobelia* plant named 'LOBZ0004' substantially as illustrated and described herein.

* * * * *